United States Patent [19]

La Viola et al.

[11] Patent Number: 4,917,116

[45] Date of Patent: Apr. 17, 1990

[54] AUTOMATIC BLOOD PRESSURE MEASURING DEVICE

[75] Inventors: John La Viola, Orange; Kevin S. Librett, Westport, both of Conn.

[73] Assignee: CAS Medical Systems, Inc., Branford, Conn.

[21] Appl. No.: 247,634

[22] Filed: Sep. 22, 1988

[51] Int. Cl.$^4$ .............................................. A61B 5/02
[52] U.S. Cl. ...................................... 128/681; 128/680
[58] Field of Search ........................ 128/672, 677–686

[56] References Cited

U.S. PATENT DOCUMENTS

| | | | |
|---|---|---|---|
| 4,543,962 | 10/1985 | Medero et al. | 128/682 |
| 4,546,775 | 10/1985 | Medero | 128/681 |
| 4,638,810 | 1/1987 | Ramsey, III et al. | 128/681 |
| 4,703,760 | 11/1987 | Miyawaki et al. | 128/681 |
| 4,754,761 | 7/1988 | Ramsey, III et al. | 128/683 |
| 4,796,184 | 1/1989 | Bahr et al. | 128/681 X |

Primary Examiner—Angela D. Sykes
Attorney, Agent, or Firm—William W. Jones

[57] ABSTRACT

A method and apparatus for determining mean blood pressure involves the use of a pre-programmed microprocessor which interprets pressure oscillation values from a pressure cuff affixed to a subject's limb. The pressure cuff is inflated to a value above apparent systolic pressure and then deflated in steps. The steps are all substantially equal mmHg declinations in cuff pressure. At each step cuff oscillation values are taken and stored. The greatest cuff oscillation and its associated cuff pressure are noted, along with the next greatest cuff oscillations and associated cuff pressures on either side of the greatest oscillation. The actual means blood pressure is then determined by forming a window adjacent to the greatest oscillation and calculating, on which side of the greatest oscillation, within the window, the means pressure is disposed.

9 Claims, 3 Drawing Sheets

AUTOMATIC BLOOD PRESSURE MEASURING DEVICE

BACKGROUND OF THE INVENTION

This application discloses an improvement of a blood pressure measuring device disclosed in copending application Ser. No. 892,848, filed Aug. 1, 1986, now U.S. Pat. No. 4,796,184 and assigned to the assignee of this application; and copending application Ser. No. 024,662, filed Mar. 11, 1987, pending and assigned to the assignee of this application. More particularly, this invention relates to an improved blood pressure measuring device which can provide more accurate determinations of mean arterial blood pressure.

The measurement of systolic, diastolic and mean arterial blood pressure values by measuring cuff pressure oscillations caused by blood vessel pulses during stepwise deflation of the cuff is a known technique. Methodology and apparatus for automatically performing this general procedure are disclosed in U.S. Pat. No. 4,349,034 granted Sept. 14, 1982 to M. Ramsey and U.S. Pat. No. 4,360,029 granted Nov. 23, 1982 to M. Ramsey. These patent disclosures relate to a technique which uses a computer controlled device to inflate a pressure cuff, stepwise deflate the cuff, measure and store cuff pressure oscillations occuring at each deflation plateau, and determine which cuff pressure oscillation was the largest. The device then identifies the cuff pressure at which the largest oscillation took place as the mean blood pressure. Provisions are made for rejecting artifact cuff pressure oscillations which can result from subject movement, accidental contact with the pressure cuff, and the like.

A device similar to that disclosed in the aforesaid patents is described in an article authored by Joseph Erlanger, M.D., published in *The Johns Hopkins Hospital Reports* Vo. XII by the Johns Hopkins Press (1904). In the Erlanger device, the cuff was automatically inflated to an initial pressure above mean, and then stepwise deflated to a pressure below mean. Cuff pressure oscillations were sensed and traced onto a rotating drum sheet by a floating pen. Artifact oscillations are apparent upon viewing the trace.

The devices described in the aforesaid patents and in the Johns Hopkins Reports all rely on the largest cuff pressure oscillation as identifying true mean blood pressure. It will be readily appreciated that such reliance is misplaced since the likelihood of the largest observed cuff pressure oscillation actually occuring exactly at the true mean blood pressure is remote. The device disclosed in copending application Ser. No. 892,848 identified above uses the greatest cuff pressure oscillation observed, along with the next greatest observed oscillation of each side thereof to calculate a parabolic curve. The zenith of the calculated curve is then used to identify true mean blood pressure. One problem that sometimes arises with the latter approach is that the calculated parabolic curves can be skewed to the wrong side of the highest observed oscillation. This is due to our observations that cuff pressure oscillations descend at a more rapid rate than they rise when the oscillations are taken at preset cuff pressure increments.

SUMMARY OF THE INVENTION

This invention uses hardware which is the same as described in the aforesaid two copending patent applications. The technique or algorithm used to identify true mean blood pressure is different. The cuff will be applied to an appendage, such as the arm, in the conventional manner, and will be inflated to an initial pressure which is determined to be above the subject's systolic blood pressure. The cuff is then automatically deflated in preset pressure increments or steps, which average about 8 mmHg. Cuff pressure oscillations are measured at each step and stored in the microprocessor's memory. After the cuff has been deflated and dumped, the computer selects the highest cuff pressure oscillation noted, and the next highest oscillation noted on both the ascending and descending sides of the highest oscillation. The deflation increments preferably average about 8 mmHg, but that average can vary when the subject's systolic pressure is very high or very low. The instrument will lower the cuff pressure in steps which never exceed 10% of the cuff pressure at the step being read. Thus when the cuff pressure is high, the deflation steps will tend to be higher, and when the cuff pressure is low, the deflation steps will tend to be lower. The average pressure deflation step is targeted at 8 mmHg, however.

The computer is programmed to assign numerical values to the cuff pressure oscillations, but there are no units to the oscillation values (other than arbitrary equal increments). The computer is also programmed to define a window around the highest noted oscillation. The window will be one-half of the pressure deflation step from the highest measured cuff pressure oscillation to either the ascending or descending side thereof. The computer will thus consider that the highest measured cuff pressure oscillation is positioned on one side of a D/2 mmHg cuff pressure window. ("D" being the size of the actual deflation step in question) Statistically, there is a greater than 99% probability that the true mean blood pressure value lies within that window. The computer determines which of the next highest oscillations identified is larger, the ascending or descending. if both are within 15% of being equal, then the highest measured oscillation is deemed to identify true mean blood pressure. When that situation exists, the computer will identify the true mean pressure as coinciding with the highest measured cuff oscillation. When the difference between the two next highest measured cuff pressure oscillations is greater than 15%, the computer will identify which is greater, and will presume that the true mean blood pressure is between the measured cuff pressure coinciding with the highest measured cuff pressure oscillation, and the measured cuff pressure coinciding with the next highest measured cuff pressure oscillation. This presumption has substantially a 99% probability of being valid. Thus the computer will have placed the true mean blood pressure value within one-half of the deflation step mmHg window. Once the location of the window has been determined, the computer will calculate the true mean arterial pressure by solving a pre-inputted equation which is set forth hereinafter. Once the true mean arterial pressure has been calculated, the computer uses the procedure described in copending application Ser. No. 892,848 to calculate true systolic and diastolic blood pressure.

It is therefore an object of this invention to provide a method and apparatus for determining the true mean arterial blood pressure of a subject.

It is a further object of this invention to provide a method and apparatus of the character described wherein the true arterial pressure is determined as lying within a range of actual measured cuff pressure values.

It is an additional object of this invention to provide a method and apparatus of the character described wherein the cuff pressure measurements are taken in descending steps at preset pressure difference intervals.

It is another object of this invention to provide a method and apparatus of the character described wherein the actual mean arterial pressure is placed within a cuff pressure window which is equal to one half of the preset pressure difference intervals. It is yet another object of this invention to provide a method and apparatus of the character described wherein the actual mean arterial pressure is calculated by solving an equation utilizing actual cuff pressure oscillation values and an empirically determined constant to determine the actual cuff pressure oscillation value which corresponds to true mean arterial pressure.

BRIEF DESCRIPTION OF THE DRAWINGS

These and other objects and advantages of the invention will become more readily apparent from the following detailed description of a preferred embodiment of the invention when taken in conjunction with the accompanying drawings, in which.

DESCRIPTION OF THE PREFERRED EMBODIMENTS

Figure 1:
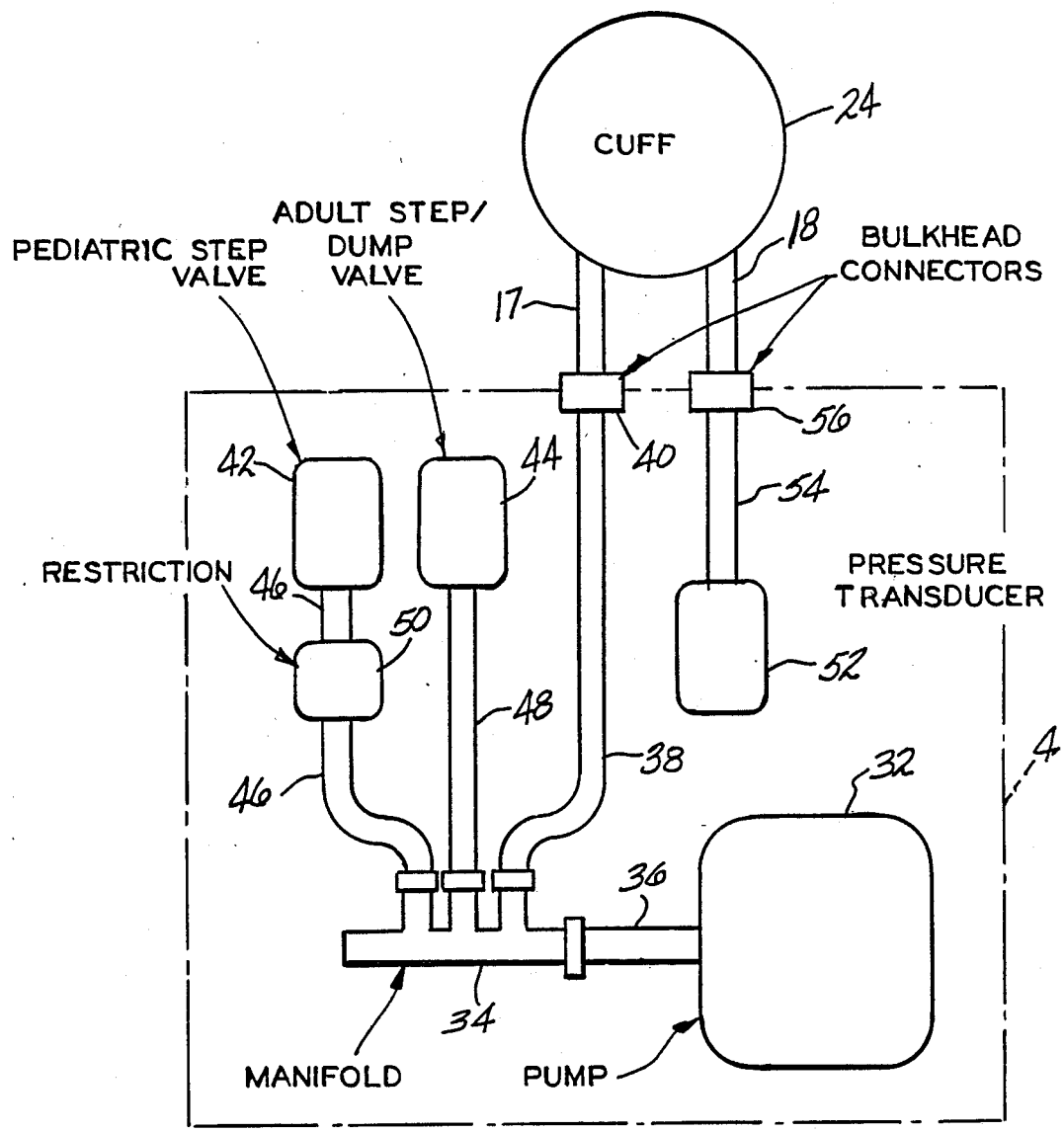
FIG. 1 is a schematic representation of the hardware used in the device of this invention.

Referring now to the drawings, FIG. 1 shows schematically the preferred hardware used in the blood pressure measuring device of this invention. The device is contained in a housing 4 (shown in phantom) and includes an arterial-occluding cuff 24 which is connected to the housing 4 by tubes 17 and 18. The tube 17 conducts air to and from the cuff 24, and the tube 18 is for measuring cuff pressure oscillations resulting from arterial pulses. Within the housing 4 is an air pump 32 connected to a manifold 34 by line 36. The manifold opens into a line 38 which connects to air tube 17 by way of bulkhead connector 40. Two air bleed valves 42 and 44 are connected to the line 38 and manifold 34 by lines 46 and 48 respectively.

The bleed valves 42 and 44 are for stepwise lowering of the air pressure in the cuff 24. The valve 42 is a smaller valve (due to the air flow restriction) which is used for pediatric subjects, and the valve 44 is a larger valve used as a final dump valve, and for adult subjects. The device preferably has the ability to distinguish between pediatric size cuffs and adult size cuffs in the same manner set forth in my copending application Ser. No. 024,662, filed Mar. 11, 1987, which is incorporated herein in its entirety for disclosure purposes. A pressure transducer 52 is disposed in the housing 4 and is connected to the tube 18 by line 54 via bulkhead 56.

The device operates generally in the same manner as set forth in copending application Ser. No. 892,848, filed Aug. 1, 1986, which is incorporated herein in its entirety for disclosure purposes. In particular, the initial inflation and subsequent stepwise deflation of the cuff 24 is performed in accordance with the software flow chart shown in FIG. 9 of the aforesaid 892,848 application.

Figure 2:
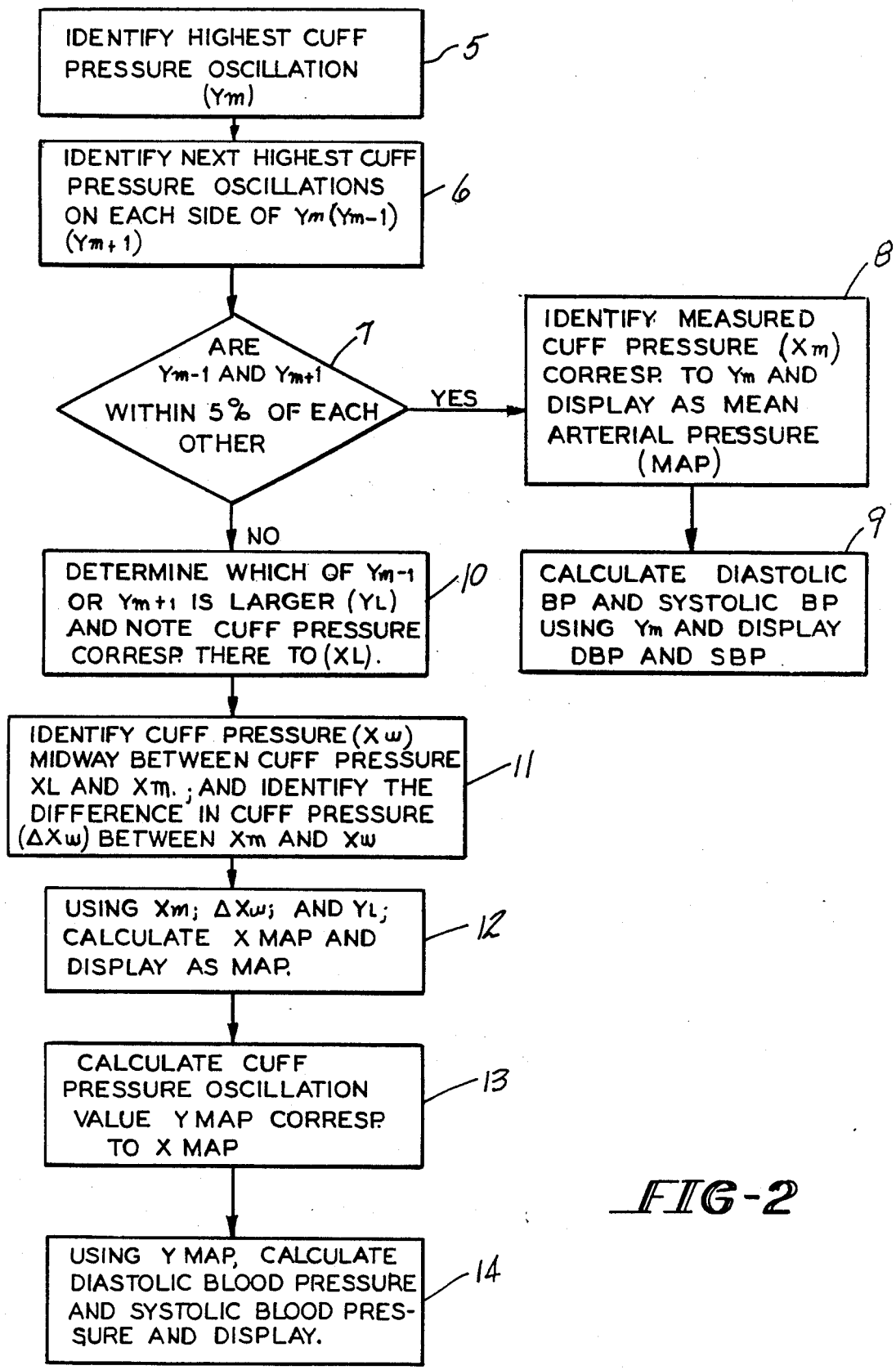
FIG. 2 is a flow chart of the software used to calculate the true mean arterial blood pressure value.

Referring now to FIG. 2, there is shown a flow chart which describes the computer program used to determine the true mean blood pressure in accordance with this invention. The first flag 5 after the cuff has been deflated, is to identify the highest cuff pressure oscillation $Y_m$ which occured during the cuff deflation procedure. The computer then at flag 6 identifies the highest cuff pressure oscillation $Y_{m-1}$ which preceded $Y_m$ during the deflation, which would be on the systolic side of $Y_m$, and the highest cuff pressure oscillation $Y_{m+1}$ which followed $Y_m$, which will be on the diastolic side of $Y_m$. At flag 7 the computer determines whether $Y_{m-1}$ and $Y_{m+1}$ are within 15% of each other. If the answer is "yes" then, per flag 8, the computer identifies the measured cuff pressure $X_m$ which corresponded with $Y_m$, and displays $X_m$ as true mean arterial blood pressure or MAP. The computer then uses $Y_m$ and the procedure set forth in USSN 892,848, to calculate the cuff pressure oscillation $Y_d$ which would correspond to diastolic pressure, and to calculate the cuff pressure oscillation $Y_s$ which would correspond to systolic blood pressure. Once $Y_d$ and $Y_s$ are known, the computer calculates the cuff pressure $X_d$ and $X_s$ corresponding thereto and displays them as true diastolic and systolic blood pressures, as per flag 9. If $Y_{m-1}$ and $Y_{m+1}$ are not within 15% of each other, then, per flag 10, the computer determines which of the two values is larger ($Y_L$) and notes the cuff pressure value $X_L$ corresponding thereto. The computer, per flag 11, then calculates the difference in cuff pressure $dX_w$, from a point which is which is midway between $X_m$ and $X_L$, and $X_m$. When $dX_w$ has been calculated, the computer, per flag 12, calculates true MAP ($X_{map}$) using a previously inputted first algorithm that is set forth hereinafter. Once $X_{map}$ has been calculated, per flag 13, the computer calculates the cuff pressure oscillation value ($Y_{map}$) which corresponds to $X_{map}$ by using a previously inputted second algorithm, also set forth hereinafter. Once $Y_{map}$ has been calculated, the computer, per flag 14, uses the procedure set forth in USSN 892,848, to calculate the cuff pressure oscillations $Y_d$ and $Y_s$ and then calculates $X_d$ and $X_s$. The true mean, diastolic and systolic blood pressures are all displayed on a digital display screen on the instrument.

The first algorithm used to calculate $X_{map}$ is as follows:

$$X_{map} = X_m + / - dX_w \{1 - [(Y_m/Y_L - 1)K]\};$$

wherein K is a constant which is empirically derived from clinical data using several factors which will indicate the maximum physiological dynamic difference between adjacent oscillations, Using the preferred 8 mmHg cuff pressure step size (during the cuff deflation procedure), the oscillation differences should be within 40% of each other, and K will equal 2.5.

The second algorithm used to calculate $Y_{map}$ is as follows:

$$Y_{map} = Y_m + (X_{map} - X_m) \, dY_{os}/dX_{os}$$

wherein: $dY_{os}$ is the difference between $Y_m$ and the next greatest Y value on the side of $Y_m$ opposite from $Y_L$; and $dX_{os}$ is the difference between $X_m$ and the next greatest X value on the side of $X_m$ opposite from $X_L$.

Figure 3:
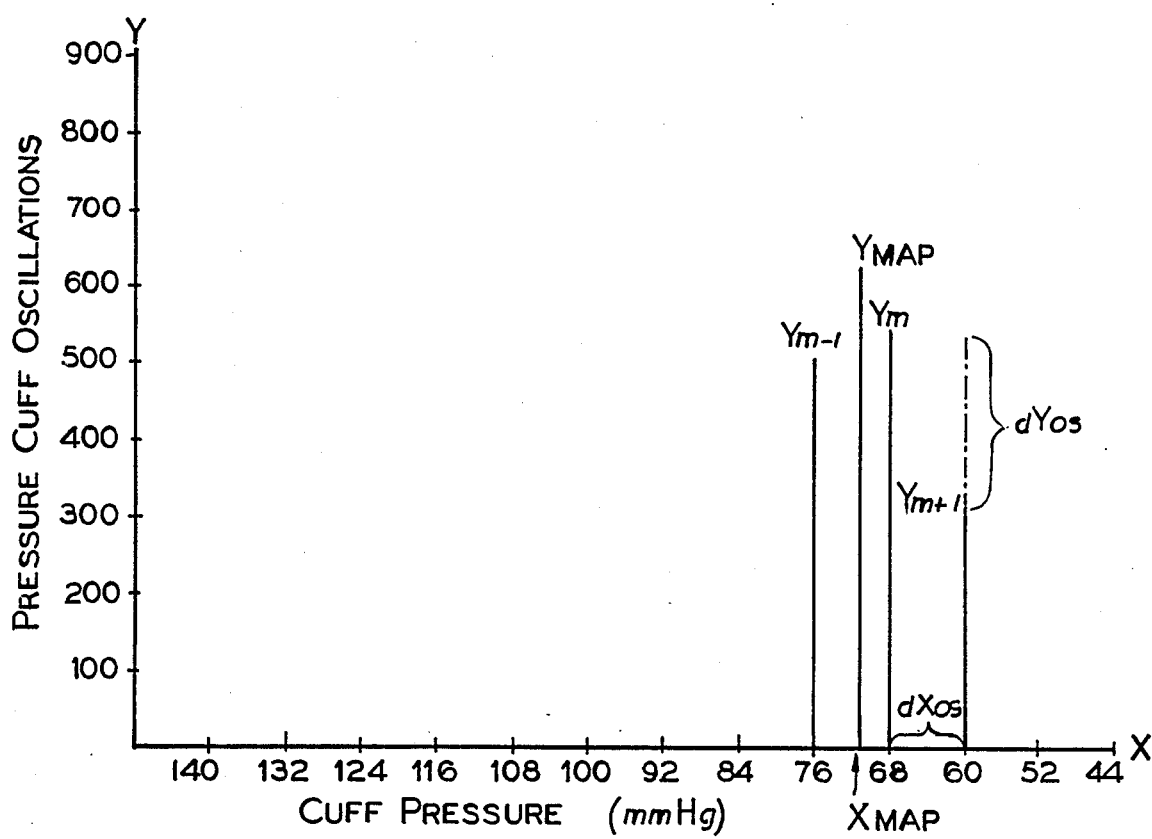
FIGS. 3 and 4 are tracings of two different cuff oscillation patterns from which mean arterial pressure (MAP) are calculated.
Figure 4:
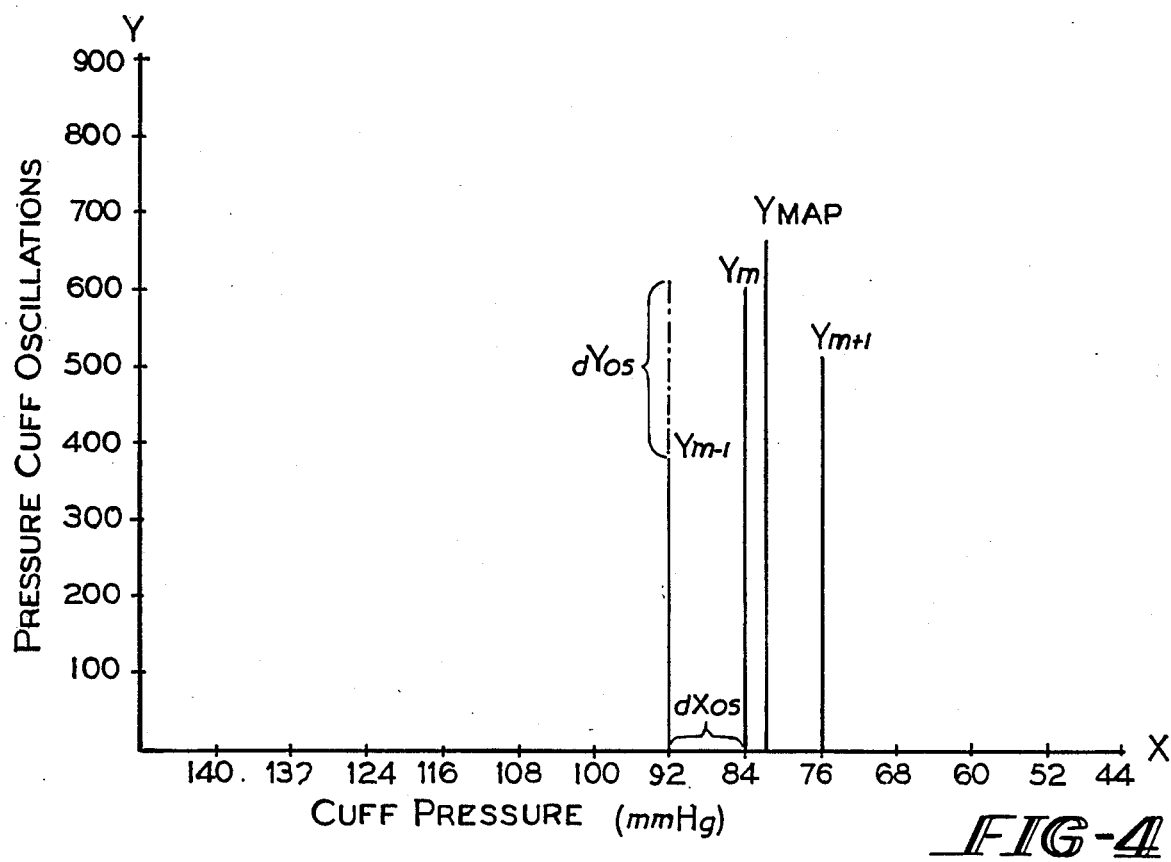

Referring now to FIGS. 3 and 4, there are shown two examples of oscillation plots from which $X_{map}$ and $Y_{map}$ will be calculated. In the FIG. 3 example, the $Y_L$ value occurs on the ascending side of the cuff pressure oscillation readings, and in the FIG. 4 example, the $Y_L$ value occurs on the descending side of the cuff pressure oscillation readings.

Referring to FIG. 3, only the specified top three cuff pressure oscillation values are shown. It will be appreciated that the Y axis denotes the cuff pressure oscillation values in pure numbers, and the X axis denotes the cuff pressure values in mmHg units. In the FIG. 3 example: $Y_m=540$; $Y_{m-1}=506$; $Y_{m+1}=311$; $X_m=68$mmHg; $X_{m-1}=76$mmHg; and $X_{m+1}=60$ mmHg.

Therefore $Y_L=506$, and $X_L=76$ mmHg, and $dX_w=4$.

Solving the equation:

$$\begin{aligned}
X_{map} &= 68 + 4\{1 - [(540/506 - 1)2.5]\}; \\
&= 68 + 4\{1 - [(1.067 - 1)2.51]\}; \\
&= 68 + 4\{1 - (.067)(2.5)\} \\
&= 68 + 4\{1 - .167\}* \\
&= 68 + 4 \times .83 \\
&= 68 + 3.3 \text{(round off to 3)} \\
&= 71; \text{ thus } X_{map} \text{ equals 71.}
\end{aligned}$$

*this number is always considered to be positive.

Solving for $Y_{map}$:

$$\begin{aligned}
Y_{map} &= Y_m + (X_{map} - X_m)dY_{os}/dX_{os} \\
&= 540 + (71 - 68) \times 229/8 \\
&= 540 + (3 \times 28.625) \\
&= 540 + 85.875(86) \\
&= 626
\end{aligned}$$

Referring now to FIG. 4, only the specified top three cuff pressure oscillations values are shown. In the FIG. 4 example: $Y_m+603$; $Y_{m-1}=390$; $Y_{m+1}=515$; $X_m=84$mmHg; $X_{m-1}=92$mmHg; and $X_{m+1}+76$mmHg.

Solving the equation:

$$\begin{aligned}
X_{map} &= X_m +/- X_w\{1 - [(Y_m/Y_L - 1)2.5]\}, \\
X_{map} &= 84 - 4\{1 - [(603/515 - 1)2.5]\}; \\
&= 84 - 4\{1 - [1.171 - 1)2.5]\}; \\
&= 84 - 4\{1 - (.171)2.5]\}; \\
&= 84 - 4\{1 - .427\} \\
&= 84 - (4 \times .573) \\
&= 84 - 2 = 82
\end{aligned}$$

Solving for $Y_{map}$:

$$\begin{aligned}
Y_{map} &= Y_m + (X_{map} - X_m)dY_{os}/dX_{os}; \\
&= 603 + (82 - 84)213/8 \\
&= 603 + (-2 \times 26)* \\
&= 603 + 52 = 655.
\end{aligned}$$

*this number is always considered to be positive

It will be readily appreciated that the blood pressure monitor of this invention provides more accurate measurements of a subject's true mean blood pressure, and the cuff pressure oscillation that would occur at the true mean blood pressure. Likewise, more accurate measurement of true diastolic and systolic pressures are also derived.

Since many changes and variations of the disclosed embodiment of the invention may be made without departing from the inventive concept, it is not intended to limit the invention otherwise than as required by the appended claims.

What is claimed is:

1. A method for determining a subject's true mean arterial blood pressure, said method comprising the steps of:
    (a) inflating a pressure cuff affixed to an appendage of the subject to a pressure which exceeds a predicted systolic blood pressure of the subject;
    (b) deflating the pressure cuff in steps, while pausing between each deflation step;
    (c) detecting, recording and storing cuff pressure oscillations at each pause between successive cuff pressure deflation steps;
    (d) continuing the steps of deflating, detecting, recording and storing, until a cuff pressure is reached which is below the subject's predicted diastolic blood pressure;
    (e) identifying the maximum cuff pressure oscillation noted and a first cuff pressure associated therewith;
    (f) identifying second and third next greatest cuff pressure oscillations on each side of said maximum oscillation, and second and third cuff pressures associated therewith; and
    (g) using data from steps (e) and (f) and calculating the percentage difference between the second and third next greatest oscillations to calculate the true mean arterial blood pressure of the subject therefrom.

2. The method of claim 1 comprising the further step of using the data gathered from steps (e), (f) and (g) to calculate the oscillation in cuff pressure corresponding to the calculated true mean arterial blood pressure.

3. The method of claim 1 further comprising the step of identifying said first cuff pressure as the mean arterial blood pressure when said second and third next greatest oscillations are within about 15% of each other.

4. The method of claim 1 further comprising the step of identifying the larger of said second and third next greatest oscillations as a target oscillation when the difference between the second and third next greatest oscillations is greater than 15%.

5. The method of claim 4 further comprising the step of identifying the cuff pressure corresponding to the target oscillation as the target cuff pressure.

6. The method of claim 5 further comprising the step of calculating one half of the difference between the target cuff pressure and the first cuff pressure and calculating true mean arterial blood pressure, Xmap by solving the equation:

$$X_{map} = X_m +/- dX_w\{1 - [Y_m(Y_L - 1)K]\};$$

wherein:
$X_m$ is the first cuff pressure;
$dx_w$ is one half of the difference between the target cuff pressure and the first cuff pressure;
$Y_m$ is the maximum cuff pressure oscillation;
$Y_L$ is the target cuff pressure oscillation; and
K is an empirically derived constant.

7. The method of claim 6 further comprising the step of calculating the cuff pressure oscillation, $Y_{map}$ which corresponds to $X_{map}$ by solving the equation:

$$Y_{map} = Y_m(X_{map} - X_m) \, dY_{os}/dX_{os};$$

wherein:
- $dY_{os}$ is the difference between $Y_{map}$ and the cuff pressure oscillation, $Y_{os}$ which is the smaller of the second and third cuff pressure oscillations; and
- $dX_{os}$ is the difference between $X_m$ and the cuff pressure, $X_{os}$ corresponding to $Y_{os}$ 8. A method for determining a subject's true mean arterial blood pressure, said method comprising the steps of:
   (a) inflating a pressure cuff affixed to an appendage of the subject to a pressure which exceeds a predicted systolic blood pressure of the subject;
   (b) deflating the pressure cuff in steps, while pausing between each deflation step;
   (c) detecting, recording and storing cuff pressure oscillations at each pause between successive cuff pressure deflation steps;
   (d) continuing the steps of deflating, detecting, recording and storing, until a cuff pressure is reached which is below the subject's predicted diastolic blood pressure;
   (e) identifying the maximum cuff pressure oscillation noted and a first cuff pressure associated therewith,
   (f) identifying second and third next greatest cuff pressure oscillations on each side of said maximum oscillation, and second and third cuff pressures associated therewith;
   (g) identifying the first cuff pressure as mean arterial pressure when the second and third cuff pressure oscillations are within 15% of each other; and
   (h) when the difference between the second and third cuff pressure oscillations is greater than 15%, calculating true mean arterial blood pressure, $X_{map}$ by solving the equation:

$$X_{map} = X_m +/- dX_w\{1 - [Y_m(Y_L - 1)K]\};$$

wherein:
- $X_m$ is the first cuff pressure;
- $dX_w$ is one half of the difference between the target cuff pressure and the first cuff pressure;
- $Y_m$ is the maximum cuff pressure oscillation;
- $Y_L$ is the target cuff pressure oscillation; and
- $K$ is an empirically derived constant.

9. The method of claim 8 further comprising the step of calculating the cuff pressure oscillation, $Y_{map}$ which corresponds to $X_{map}$ by solving the equation:

$$Y_{map} = Y_m(X_{map} - X_m) \, dY_{os}/dX_{os};$$

wherein:
- $dY_{os}$ is the difference between $Y_{map}$ and the cuff pressure oscillation, $Y_{os}$ which is the smaller of the second and third cuff pressure oscillations; and
- $dX_{os}$ is the difference between $X_m$ and the cuff pressure, $X_{os}$ corresponding to $Y_{os}$.

* * * * *